United States Patent
Wild et al.

(10) Patent No.: US 9,891,166 B2
(45) Date of Patent: Feb. 13, 2018

(54) FIBER OPTIC SENSOR FOR MEASUREMENT OF CARBON DIOXIDE

(71) Applicant: UVic Industry Partnerships Inc., Victoria (CA)

(72) Inventors: Peter M. Wild, Victoria (CA); Thomas M. Fyles, Victoria (CA); David A. Risk, Antigonish (CA); David A. Sinton, Toronto (CA); Bo Bao, Toronto (CA); Luis Melo, Victoria (CA); Martin B. G. Jun, Victoria (CA); Geoff Burton, Victoria (CA)

(*) Notice: Subject to any disclaimer, the term of this patent is extended or adjusted under 35 U.S.C. 154(b) by 0 days.

(21) Appl. No.: 15/032,794

(22) PCT Filed: Nov. 3, 2014

(86) PCT No.: PCT/CA2014/000781
§ 371 (c)(1),
(2) Date: Apr. 28, 2016

(87) PCT Pub. No.: WO2015/061886
PCT Pub. Date: May 7, 2015

(65) Prior Publication Data
US 2016/0252450 A1    Sep. 1, 2016

Related U.S. Application Data

(60) Provisional application No. 61/899,821, filed on Nov. 4, 2013.

(51) Int. Cl.
*G01D 5/353*    (2006.01)
*G01N 21/45*    (2006.01)
(Continued)

(52) U.S. Cl.
CPC ............ *G01N 21/45* (2013.01); *E21B 47/10* (2013.01); *E21B 47/123* (2013.01);
(Continued)

(58) Field of Classification Search
CPC ............... G01D 5/353; G01D 5/35303; G01D 5/35316; G01N 21/45
(Continued)

(56) References Cited

U.S. PATENT DOCUMENTS 5,005,005 A * 4/1991 Brossia .................. B64D 15/20
                                                                250/573
5,864,641 A    1/1999 Murphy et al.
(Continued)

FOREIGN PATENT DOCUMENTS

CA        2830281        10/2011
KR     1020120042663      5/2012

OTHER PUBLICATIONS

Benson et al., Overview of Monitoring Requirements for Geological Storage Projects, IEAGHG Report No. PH4/29, 89 pages (Nov. 2004).
(Continued)

*Primary Examiner* — Jonathan Hansen
(74) *Attorney, Agent, or Firm* — Klarquist Sparkman, LLP (57) ABSTRACT

Fiber optic sensors include sensor regions in which an optical phase is modulated by an analyte to be detected. A long period fiber grating (LPG) is coupled to a coating that is arranged to selectively interact with the analyte. The resulting phase change is detected based on a transmission spectrum associated with the LPG so that analyte is detected and quantified. A plurality of such sensors is distributed along a fiber to form a sensor array that can be situated to detect analyte at a plurality of discrete regions.

21 Claims, 8 Drawing Sheets

(51) Int. Cl.

| | | |
|---|---|---|
| *E21B 47/10* | (2012.01) | |
| *G01V 9/00* | (2006.01) | |
| *E21B 47/12* | (2012.01) | |
| *G01N 21/77* | (2006.01) | |
| *G01N 33/18* | (2006.01) | |

(52) U.S. Cl.
CPC ........... *G01N 21/774* (2013.01); *G01N 33/18* (2013.01); *G01V 9/007* (2013.01); *G01N 2021/458* (2013.01); *G01N 2201/062* (2013.01); *G01N 2201/088* (2013.01); *G01N 2201/12* (2013.01)

(58) Field of Classification Search
USPC .................................................. 356/481, 478
See application file for complete search history.

(56) References Cited

U.S. PATENT DOCUMENTS

| | | | | |
|---|---|---|---|---|
| 7,489,835 | B1* | 2/2009 | Xia | G01N 21/774 385/12 |
| 2011/0211795 | A1* | 9/2011 | Xia | G01D 5/35316 385/123 |
| 2012/0081696 | A1* | 4/2012 | Boersma | G01D 5/268 356/73.1 |
| 2013/0084037 | A1* | 4/2013 | Xia | B82Y 20/00 385/12 |
| 2013/0099957 | A1 | 4/2013 | Goodwin et al. | |

OTHER PUBLICATIONS

Gouveia et al., "Measurement of $CO_2$ using refractometric fiber optic sensors," SENSIG'10/Materials'10—Proceedings of the $3^{rd}$ WSEAS international conference on advances in sensors, signals and materials, pp. 169-173 (2010).

International Search Report and Written Opinion from International Application No. PCT/CA2014/000781, dated Jan. 22, 2015, 8 pages.

Orghici et al., "Fiber optic evanescent field sensor for detection of explosives and $CO_2$ dissolved in water," *Applied Physics B Laser and Optics*, 90:355-360 (Jan. 2008).

Chen et al., "A multi-D-shaped optical fiber for refractive index sensing," *Sensors*, 10:4794-4804 (2010).

David et al., "Simultaneous in situ measurement of temperature and relative humidity in a PEMFC using optical fiber sensors," *Journal of the Electrochemical Society*, 157:B1173-B1179 (2010).

Dennison et al., "Enhanced sensitivity of an in-fibre Bragg grating pressure sensor achieved through fibre diameter reduction," *Meas. Sci. Technol.*, 19:125301-125311 (2008).

Erickson et al., "Nanobiosensors: Optofluidic, electrical and mechanical approaches to biomolecular detection at the nanoscale," *Microfluid Nanofluidics*, 4:33-52 (2008).

Liang et al., "Highly sensitive fiber Bragg grating refractive index sensors," *App. Phys. Letters*, 86:151122-1-151122-3 (2005).

Martin et al., "A carbon dioxide flux generator for testing infrared gas analyzer-based soil respiration systems," *Soil Sci. Soc. Am. J.*, 68:514-518 (2004).

McKnee, "Discussion paper from the task force for identifying gaps in $CO_2$ monitoring and verification of storage," Carbon Sequestration Leadership Forum (2005).

Men et al., "A multiplexed fiber Bragg grating sensor for simultaneous salinity and temperature measurement," *J. Appl. Phys.*, 103:053107-1-053107-7 (2008).

Nickerson et al., "A numerical evaluation of chamber methodologies used in measuring the $\delta^{13}C$ of soil respiration," *Rapid Commun. Mass Spectrom.*, 23:2802-2810 (2009).

Pearce et al., "Monitoring technologies for the geological storage of $CO_2$," UK Dept. of Trade and Ind. Tech. Status Review Report. No. DTI/Pub URN 05/1032 (2005).

Preston et al., "IEA GHG Weyburn $CO_2$ monitoring and storage project," *Fuel Proc. Tech.*, 86:1547-1568 (2005).

Schuster et al., "Sensors and instruments for oceanic dissolved carbon measurements," *Ocean Sci.*, 5:547-558 (2009).

United States Dept. of Energy/National Energy Technology Laboratory, Monitoring, verification, and accounting of $CO_2$ stored in deep geologic formations (Report No. U.S. DOE/NETL-311/081508) (2009).

Wildenborg et al., "Large-scale $CO_2$ injection demos for the development of monitoring and verification technology and guidelines (CO2ReMoVe)," *Energy Procedia*, 1: 2367-2374 (2009).

Zhou et al., "Implementation of optical chemsensors based on HF-etched fibre Bragg grating structures," *Meas. Sci. Technol.*, 17:1140-1145 (2006).

\* cited by examiner

FIBER OPTIC SENSOR FOR MEASUREMENT OF CARBON DIOXIDE

CROSS REFERENCE TO RELATED APPLICATIONS

This is the U.S. National Stage of International Application No. PCT/CA2014/000781, filed Nov. 3, 2014, which was published in English under PCT Article 21(2), which claims the benefit of U.S. Provisional Application No. 61/899,821, filed Nov. 4, 2013.

FIELD

The disclosure pertains to fiber-optic sensors.

BACKGROUND

Technologies exist to detect and measure $CO_2$ volumes, concentrations and fluxes in deep geologic, shallow subsurface, marine and atmospheric environments. These technologies include seismic, electromagnetic, gravimetric, geochemical, geophysical and optical methods. Principal among the applications of these monitoring technologies are: (1) enhanced oil recovery operations and (2) measurement of $CO_2$ emissions from natural landscapes to quantify emissions due to landscape use and to demonstrate compliance with international agreements. There is, in addition, an emerging application for Monitoring, Measurement and Verification (MMV) of $CO_2$ geosequestration sites both during injection and during long term storage periods.

Existing technologies are not well suited to measurements at densely spaced, shallow sub-surface sampling sites, the detection and monitoring of $CO_2$ fluxes from the vadose zone to the atmosphere the identification of leaks along wellbores the detection of dissolved $CO_2$ seepage into subaqueous environments and the detection of leakage during injection or post-injection from subsea wells and formations. In addition to these deficiencies, the capital and operating costs of conventional MMV technologies for geologic $CO_2$ storage are impractically high. Thus, current methods cannot be economically deployed for distributed MMV of many of the possible leakage paths for $CO_2$ in geologic storage, and improved approaches are needed.

SUMMARY

Single and multiple sensors and sensor systems include one or more optical fibers. In some examples, sensors are responsive to the refractive index of a medium that surrounds (as used herein, "surrounding refractive index" or "SRI") the fiber and thereby to the concentration of an analyte such as $CO_2$ in the medium (such as water, seawater, or air). The sensors are interrogated by a device that is located at one end of the optical fiber. Interrogation devices can include one or more light sources such as diode lasers or other coherent sources, LEDs, or incoherent sources such as arc lamps or quartz-halogen bulbs. Optical radiation that is returned to an interrogation device is directed to one or more optical detectors such as photodiodes, CCD arrays, photomultipliers or other detectors. In some examples, wavelength dependent devices such as gratings or dichroic filters are used to separate various wavelength components so that one or more detectors receive a corresponding wavelength component. Multiple wavelengths can be simultaneously or sequentially applied and/or detected. In some examples, fibers and sensor systems are deployed in an array so as to provide coverage of a large region of a surface, subsurface, or subsea environment. Refractive indices can be detected using sensors that include in-fiber Bragg gratings, long period gratings, Fabry-Perot interferometers, Mach-Zehnder interferometers, or other interferometric devices.

Sensors can be integrated into various types of optical fibers, including single mode fiber and photonic crystal fiber. These fibers can be integrated into cables that are deployed above, adjacent to, or in formations in which $CO_2$ is stored or concentrations of other analytes are of interest.

The foregoing and other objects, features, and advantages of the disclosed technology will become more apparent from the following detailed description, which proceeds with reference to the accompanying figures.

DETAILED DESCRIPTION

As used in this application and in the claims, the singular forms "a," "an," and "the" include the plural forms unless the context clearly dictates otherwise. Additionally, the term "includes" means "comprises." Further, the term "coupled" does not exclude the presence of intermediate elements between the coupled items.

The systems, apparatus, and methods described herein should not be construed as limiting in any way. Instead, the present disclosure is directed toward all novel and nonobvious features and aspects of the various disclosed embodiments, alone and in various combinations and subcombinations with one another. The disclosed systems, methods, and apparatus are not limited to any specific aspect or feature or combinations thereof, nor do the disclosed systems, methods, and apparatus require that any one or more specific advantages be present or problems be solved. Any theories of operation are to facilitate explanation, but the disclosed systems, methods, and apparatus are not limited to such theories of operation.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

In some examples, values, procedures, or apparatus' are referred to as "lowest", "best", "minimum," or the like. It will be appreciated that such descriptions are intended to indicate that a selection among many used functional alternatives can be made, and such selections need not be better, smaller, or otherwise preferable to other selections.

The disclosed examples are described with reference to fibers having circular cross-sections, but fibers having other cross-sections can be used such as square, rectangular, ellipsoid, ovoid, polygonal or other shapes. Fibers are conveniently defined by core and cladding materials having prescribed refractive index difference so as to define one or more optical modes that propagate in the fiber. Various fiber types can be used such as single mode, few mode, or multimode fibers. Fiber materials can include glasses, plastics, or other transparent materials. Photonic crystal fibers can also be used.

Figure 1:
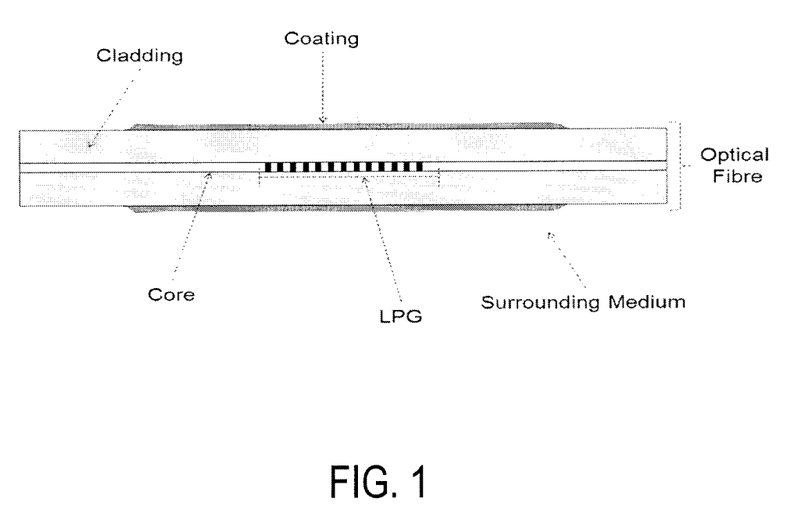
FIG. 1 is a sensor that includes a coated long-period fiber grating (LPG).

In representative examples, sensors comprise optical fibers that include one or more long period gratings (LPGs) as shown in FIG. 1. LPGs typically have periods of between about 0.02 mm and 10 mm, 0.05 mm and 5 mm, or 0.1 mm and 1 mm. LPGs can be photoinduced and couple optical radiation propagating in a fundamental mode into one or more co-propagating cladding modes. Attenuation of optical radiation in the cladding modes results in a wavelength dependent transmission spectrum that is a function of LPG period. Sensor systems based on LPGs return optical radiation transmitted by an LPG to a detection system for measurement of the associated transmission spectrum. A fiber loop can be used, or a reflector provided at a fiber end to return the optical radiation.

As shown in FIG. 1, an optical fiber includes an LPG defined in a fiber core that is enclosed by a fiber cladding. A coating is situated on the cladding in a fiber region corresponding to the LPG. A medium of interest (such as a medium that contains an analyte of interest) contacts the coating (or at least a portion thereof) and can contact a portion of a cladding exterior surface as well. Typically, in the region of the LPG, the outer cylindrical surface of the fiber is coated with a specified thickness of a specified material. This coating can be selected to act in several ways, as described below, to introduce or to enhance sensitivity of the wavelength and/or the amplitude of the attenuation band in the transmitted spectrum of the LPG to a concentration of the target species (e.g., $CO_2$).

Several different sensor types are described below. These sensor types are not mutually exclusive, and a particular sensor can be associated with one or more or all of the following types.

EXAMPLE 1

Enhanced Evanescent Field Coupling

In some examples, the coating material has a refractive index that is higher than the refractive index of the cladding (i.e. the outer surface) of the optical fiber. This coating enhances coupling of evanescent fields to a medium that surrounds the fiber or surrounding refractive index (SRI). This enhanced coupling increases the sensitivity of both the wavelength and the amplitude of the attenuation band in the transmitted spectrum of the LPG to the SRI. The refractive index of an aqueous solution of $CO_2$ is a function of the concentration of $CO_2$ and, therefore, the coated LPG acts as a sensor for $CO_2$ concentration. The thickness of the coating is selected so as to optimise the sensitivity of this sensor.

In one example, a diamond-like carbon coating is situated on the fiber near the LPG. This coating leads to the enhancement of the evanescent field in the medium that surrounds the fiber which leads to the significant increase of the sensitivity of the sensor. This coating has an additional important feature which consists of acting as a protection layer by hermetically protecting otherwise exposed regions of the fiber to the penetration of water which is known to cause degradation of fiber signals over long monitoring periods.

EXAMPLE 2

Reversible Coating Absorption

A coating material can absorb a target species (such as $CO_2$) from the surrounding medium in a reversible manner. The equilibrium concentration of the target species in the coating material is generally a monotonic function of the concentration of the target species in the surrounding medium. The refractive index of the coating material is a function of the concentration of the target species in the coating material. The wavelength, amplitude, and/or shape of an attenuation band in a transmission spectrum of an LPG are also generally monotonic functions of the refractive index of the coating. As a result, the wavelength and amplitude of the attenuation band in the transmission spectrum of the LPG are monotonic functions of the concentration of the target species in the surrounding medium.

A representative example of a sensor of this type includes a polystyrene coating on an optical fiber in the region of an LPG. The coating physically absorbs $CO_2$, resulting in a change of refractive index which the optical fiber transduces to an analytically useful signal. Another example of a sensor of this type includes a coating of an acrylate or acrylamide copolymer containing tertiary amine sites which in the presence of $CO_2$ and water vapor reversibly form a salt species according to:

$$\text{Coating-NR}_2 + \text{H}_2\text{O} + \text{CO}_2 \rightarrow \text{Coating-NH}^+\text{R}_2\text{HCO}_3^-$$

The resultant salt has an altered refractive index which the optical fiber LPG transduces to the analytically useful signal as a change in an LPG transmission spectrum.

EXAMPLE 3

Absorption Inducing Strain

Sensors can also be configured to be responsive to strain resulting from the absorption of a target species. In one example, a coating material absorbs the target species (i.e. $CO_2$) from the surrounding medium in a reversible manner. The equilibrium concentration of the target species in the coating material is a monotonic function of the concentration of the target species in the surrounding medium, and the density of the coating material is a monotonic function of the concentration of the target species in the coating material. As a result, the density of the coating material is a monotonic function of the concentration of the target species in the surrounding medium. Changes in the density of the coating are transduced to axial strain in the optical fiber in the region of the LPG by adhesion of the coating to fiber as shown in FIG. 1. The wavelength and amplitude of the attenuation band in the transmission spectrum of the LPG are monotonic functions of the fiber strain in the region of the LPG. As a result, the wavelength and amplitude of the attenuation band in the transmission spectrum of the LPG are monotonic functions of the concentration of the target species in the surrounding medium.

In some examples, a sensor of this type is based on the same chemical principle as given above, i.e., a copolymer of acrylamide containing tertiary amine sites reacts with $CO_2$ and water to produce salts. The formation of the salt causes the coating to swell, leading to the axial strain in the optical fiber.

EXAMPLE 4

Encapsulated Sensors

Figure 2:
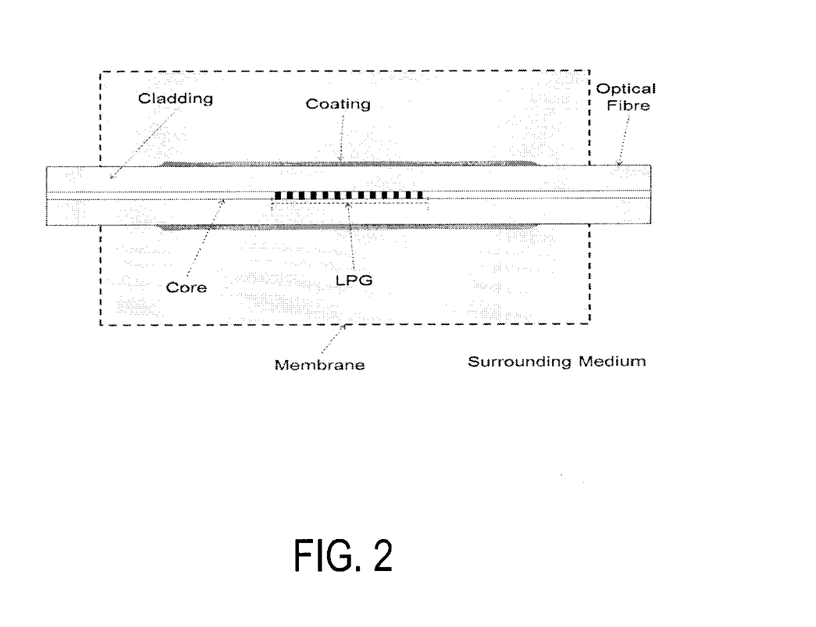
FIG. 2 is a sensor that includes a coated LPG with membrane encapsulation.

In any of the above configurations, a coated LPG can be encapsulated in a selective membrane, as shown in FIG. 2. The membrane can be configured to be selectively permeable to the target species or to be selectively impermeable to a species which competes with the target species. In either case the membrane enhances the selectivity and specificity of the sensor for the target species by eliminating competing species that may add to or interfere with the desired signal. For example, the reversible $CO_2$ reaction given above is potentially subject to interference by $H_2S$. A polymer membrane having a selectivity for $CO_2$ over $H_2S$ then results in a sensor that is responsive to $CO_2$ with no or reduced $H_2S$ interference.

Figure 3:
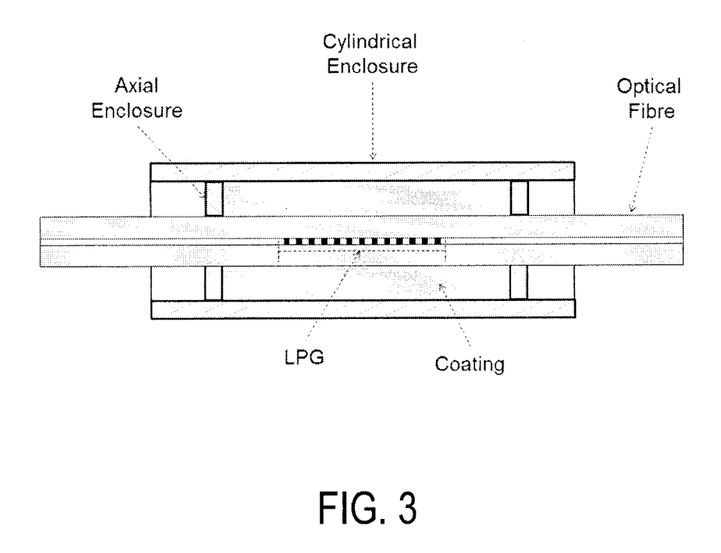
FIG. 3 is a sensor that includes a coated LPG enclosed in a structure so as to communicate density changes in the coating to axial strain in the LPG.

An alternative configuration of a sensor includes a structure that encloses the LPG. As shown in FIG. 3, the surrounding structure is porous so as to allow the surrounding medium to come into contact with the coating material. The structure is filled with a coating material and deforms axially as the coating swells or shrinks in response to the presence of an analyte (for example, $CO_2$). In the example of FIG. 3, the axial enclosures are fixed to the fiber but are free to move with respect to the cylindrical enclosure which is relatively rigid. As the coating material volume changes, the axial enclosures move and this motion is applied to the fiber as strain. This strain is transduced by the LPG into changes in wavelength and amplitude of spectral features in an attenuation band in a transmission spectrum. In an alternative configuration, the enclosure incorporates a membrane that functions, as described above, to provide selectivity for or against a selected analyte.

Figure 4:
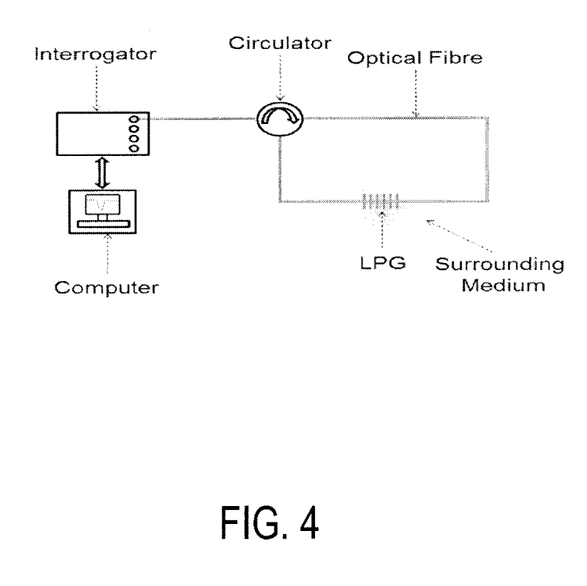
FIG. 4 illustrates a representative interrogation scheme for an LPG-based sensor.

In the sensor configurations disclosed above based on LPGs, a transmission spectrum of the LPG is modulated by an analyte and is used to estimate analyte concentration. A sensor system configured to estimate analyte concentrations is illustrated in FIG. 4. An optical system (an "interrogator") couples optical radiation at a plurality of frequencies to an optical circulator that couples the optical radiation to an optical fiber that includes an LPG that is situated in a medium of interest. Optical radiation transmitted by the LPG is returned to the optical circulator and then to the interrogator. The interrogator includes one or more detectors, photodetector amplifiers and other processing circuitry so as to produce an electrical signal corresponding to LPG transmission as a function of wavelength. An array sensor and a diffraction grating can be used, or a laser source can be configured to produce optical radiation at a time-varying wavelength by changing laser temperature or drive current. In one example, an LED is used to produce optical radiation having a sufficient spectral width for detecting changes in LPG transmission as a function of wavelength.

A computer such as a personal computer, handheld computer, tablet, or other computing device is configured to detect an analyte or estimate an analyte concentration based on changes in an LPG transmission spectrum. The computer also includes non-transitory storage such as RAM, ROM, a hard disk, or other devices that store computer-executable instructions for processing transmission spectra, as well as storage of acquired transmission spectra. In addition, the computer can control operation of the interrogator. In some cases, the computer communicates measurement results via a wide area network.

Sensor configurations as disclosed above can also be implemented using alternative fiber-based optical devices in place of the LPG. For example, in-fiber Bragg gratings (FBGs) can be used. FBGs are generally written in fibers that are etched to a reduced diameter so as to enhance interaction of evanescent fields with a surrounding refractive index. Photonic crystals fibers can be used and spliced to conventional fibers such as single mode fibers to form balanced or unbalanced Mach-Zehnder interferometers that are sensitive to refractive index changes.

Other types of interferometers can be used to detect phase changes associated with axial stress or coating changes in response to exposure to a selected analyte.

Figure 5:
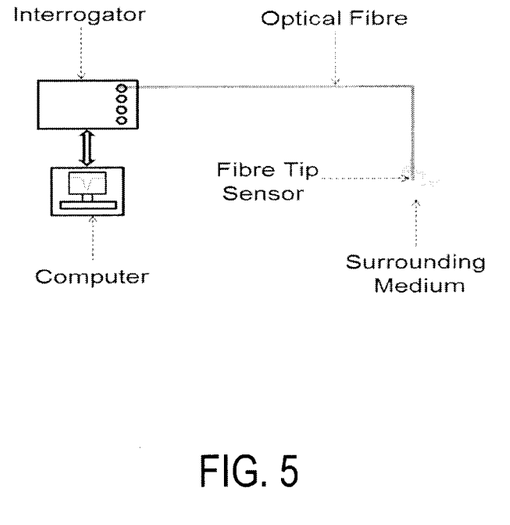
FIG. 5 illustrates a fiber tip sensor and a related method of interrogation.

In still further examples, sensors can be configured to distinguish between different phases and different species. For example, in the context of subsea injection of $CO_2$, such sensors can distinguish between an aqueous salt solution (e.g., seawater or brine) and gaseous, liquid or supercritical $CO_2$, based on differences in the refractive indices of these substances. For this application, an alternative sensor includes an optical fiber whose distal end or "tip" comprises a sensing region, as shown in FIG. 5. A portion of an optical beam propagating toward the distal end of the fiber is reflected at an interface between the fiber tip and a medium surrounding the fiber and returned into the fiber core. The fiber tip may be coated with a hydrophobic material (e.g., n-Octadecyltriethoxysilane) to prevent adhesion of aqueous solutions. The intensity of any reflected light is a function of the refractive index of the surrounding medium and, therefore, interrogation of this reflected light signal is required, as shown in FIG. 5.

EXAMPLE 5

Ocean Measurements

Figure 6:
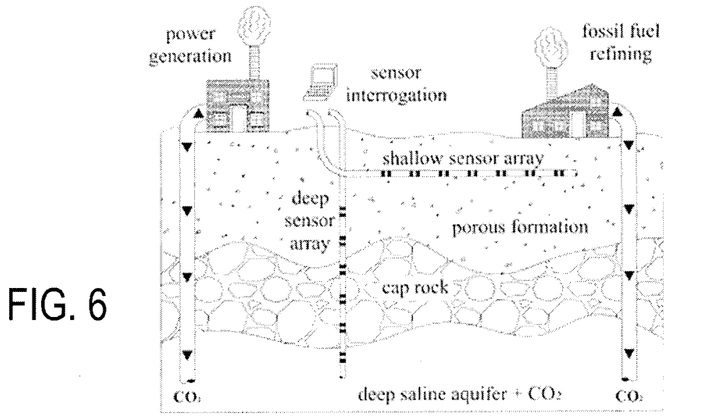
FIG. 6 is a schematic of distributed sensing and centralized interrogation with multiple fiber arrays in field-scale sequestration operations.

An example implantation of such sensor systems is shown in FIG. 6. A detection and reporting system is situated at a surface location, and fibers that include a plurality of sensor regions are configured to serve as a deep sensor array and a shallow sensor array. The fibers are generally configured as fiber loops so that transmitted optical radiation can be detected, but as noted above, a reflector can be provided at a fiber end so that optical radiation is reflected back through the sensor regions so that double pass transmission spectra can be obtained.

Figure 7A:
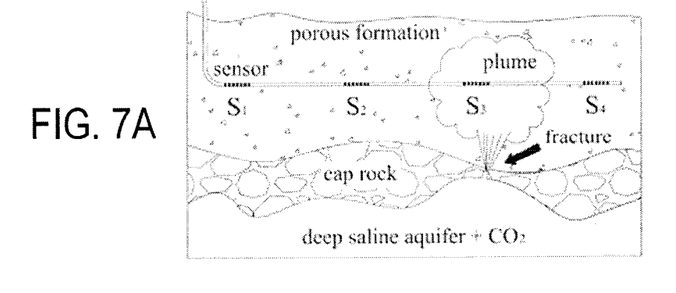
FIG. 7A illustrates four multiplexed fiber Bragg grating (FBG)-based $CO_2$ sensors deployed for detection of leakage from a saline aquifer.
Figure 7B:
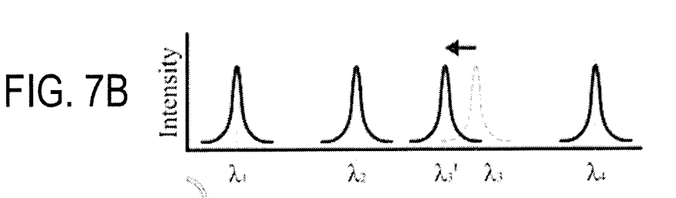
FIG. 7B is a plot showing a shift in a Bragg wavelength ($\lambda 3$) of an FBG located in a spreading plume.

FIGS. 7A-7B illustrate operation of a shallow sensor array that is coupled to a plume. As shown in FIG. 7A, a sensor region (S3) is situated within the analyte plume. FIG. 7B shows a spectral shift of the spectrum of sensor S3 associated with the presence of analyte in the plume. Spectra of other sensor regions (S1, S2, S4) are unchanged, so that detection at sensor S3 permits location of the plume as well as assessment of analyte concentration.

Figure 8:
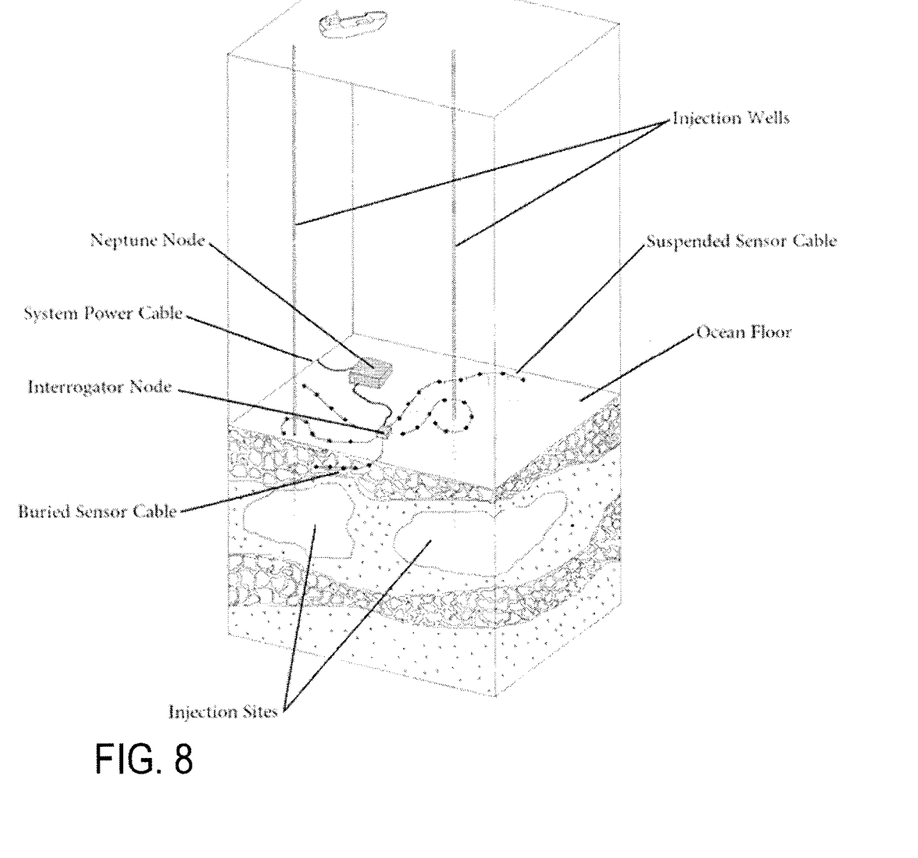
FIG. 8 illustrates deployment of a sensor array as disclosed, on and above the sea floor.

FIG. 8 illustrates a sensor system situated at an ocean floor. A plurality of sensor cables (each with one or more sensor regions) is coupled to an interrogator that is powered by a node at the ocean floor. The sensor cables can be suspended about the ocean floor, buried in the ocean floor, situated on the ocean floor, or extend vertically from the ocean floor. The interrogation system can be coupled to communicate with a surface vessel with one or more electrical or optical cables, or an acoustic transceiver. Other sensors such as temperature or pressure sensors can be provided so that optical sensor measurements can be at compensated to reduce pressure and temperature effects as desired.

EXAMPLE 6

Additional Sensor Configurations

Figure 9:
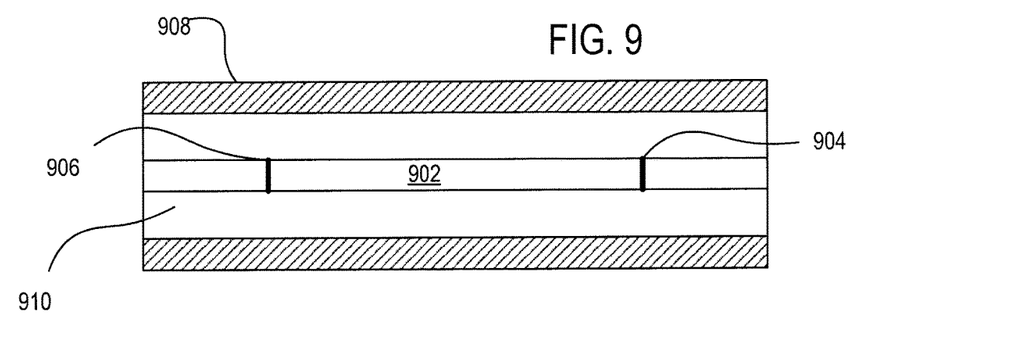
FIG. 9 illustrates a Fabry-Perot interferometer-based sensor responsive to absorption of an analyte in a coating situated on a fiber cladding, such as a reduced diameter fiber cladding.

Referring to FIG. 9, a Fabry-Perot sensor region 900 included a fiber core section 902 that is terminated with reflective regions 904, 906. Reflectances of the regions 904, 906, and a length of the fiber section 902 can be selected to provide a desired Fabry-Perot resonator finesse and free spectral range. The fiber core section 902 is surrounded by a fiber cladding 910 that is in contact with a sensor coating 908. Absorption of analyte in the sensor coating 908 can produce phase changes for optical radiation propagating in the core section 902 so that the transmission or reflectance spectrum of the Fabry-Perot resonator defined by the core section 902 and the reflectors 904, 906 is changed. Detection of the changed spectrum permits evaluation of analyte concentration.

Figure 10:
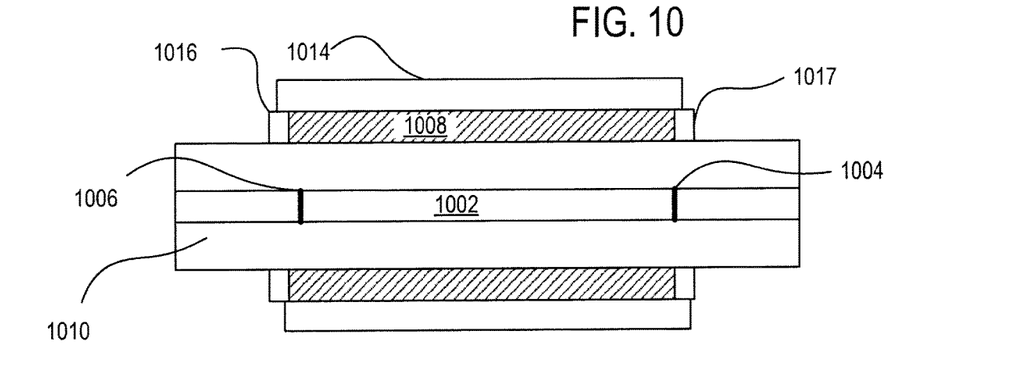
FIG. 10 illustrates a Fabry-Perot interferometer-based sensor responsive to an axial strain.

FIG. 10 illustrates an alternative Fabry-Perot sensor region that includes a fiber core section 1002 that is terminated with reflective regions 1004, 1006. Reflectances of the regions 1004, 1006, and a length of the fiber section 1002 can be selected to provide a desired Fabry-Perot resonator finesse and free spectral range. The fiber core section 1002 is surrounded by a fiber cladding 1010 that is in contact with a sensor coating 1008 that is confined by a radial enclosure 1014 and axial enclosures 1016, 1017. The enclosure 1014 is referred to as a radial enclosure but can have an arbitrary cross-section such as polygonal or ovoid and is generally configured so that coating dimensional changes are coupled to the axial enclosures 1016, 1017. Absorption of analyte in the sensor coating 1008 can produce phase changes for optical radiation propagating in the core section 1002 due to axial strain. The transmission or reflectance spectrum of the Fabry-Perot resonator defined by the core section 1002 and the reflectors 1004, 1006 is changed in response to the axial strain. Detection of the changed spectrum permits evaluation of analyte concentration.

Figure 11:
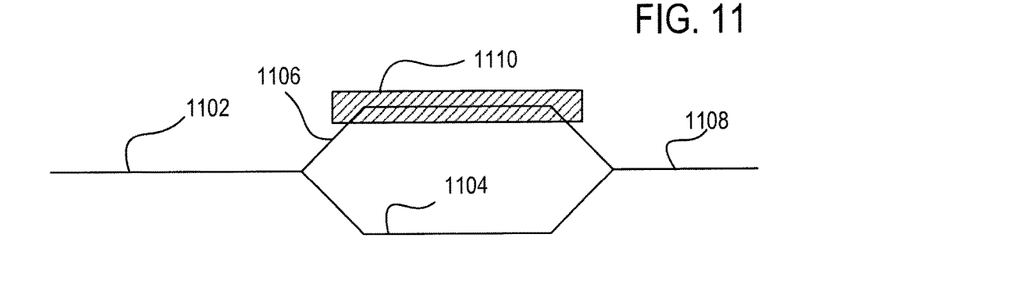
FIG. 11 illustrates a portion of a Mach-Zehnder -based fiber sensor that includes a photonic crystal fiber.

Sensors can also be based on multipath interferometers such as Mach-Zehnder interferometers. As shown in FIG. 11 an interferometer 1100 includes an input fiber section 1102, a first branch 1104, a second branch 1106, and an output section 1108. These sections are generally single mode fiber sections, but can be conventional silica fibers or other types of fibers such as photonic crystal fibers, or combinations of such fibers. An absorbing coating 1110 is situated so as to interact with optical radiation propagating in the second branch 1106 so as to permit analyte concentration estimation. The coating 1110 can be configured to produce strain, interact with evanescent fields, or otherwise interact with optical radiation in the branch 1106. In FIG. 11, the second branch 1106 and the first branch 1104 are shown as having about the same optical path length (i.e., the Mach-Zehnder interferometer is balanced), but unequal paths can be used, particularly to increase interaction lengths of the coating 1110 and the second branch 1106.

EXAMPLE 7

Sensor Arrays

In some examples, a plurality of discrete measurement devices (sensor regions) is configured to form arrays that can provide coverage of a large region of a surface, subsurface, or a subsea environment at a plurality of discrete locations. In some cases, structures such as coatings are coupled so as to interact with propagating optical radiation in the sensor regions. In some cases, the coatings preferentially reversibly or irreversibly bind or absorb substances to be detected. Membranes or other selective coatings or enclosures can be situated so that only selected substance are directed to sensor regions. In convenient examples, coatings are applied to fiber claddings, and membranes situated about the coatings.

In representative examples, the sensor regions are at fixed positions along a length of an optical fiber and are configured to be sensitive to a total concentration of carbon dioxide, carbonate, bicarbonate and/or carbonic acid in an aqueous solution. In some examples, the sensor regions are configured so that contact with gaseous, liquid or supercritical $CO_2$, aqueous saline solutions and liquid or gaseous hydrocarbons can be distinguished. In some cases, the sensor regions are responsive to refractive index changes in a medium that is in contact with a sensor region. In representative examples, long period gratings are used to define sensor regions, and transmitted optical radiation is detected to estimate analyte concentration. In other examples, in-fiber Bragg gratings are situated in one or more optical fibers that are modified or shaped so that evanescent fields of the optical radiation in a fiber core interact with a medium that surrounds the fiber. In still further examples, sensor regions comprise Mach-Zehnder interferometers that comprise photonic crystal fiber sections spliced to single mode fiber. Sensor regions can be coated with a material or materials that enhance sensitivity to refractive index, or encapsulated in a material that changes optical properties when in contact with carbon dioxide, carbonate, bicarbonate and carbonic acid in an aqueous solution or gaseous carbon dioxide. The encapsulating material can serve as a filter that allows carbon dioxide, carbonate, bicarbonate and carbonic acid to pass preferentially from the media that surrounds the sensor region to the sensor region. The encapsulating material can comprise or be enclosed within a membrane that is selectively permeable to $CO_2$ among other gases, or selectively permeable to carbonate or bicarbonate among other anions, or selectively permeable to carbonic acid among other acids.

In convenient examples, sensor regions are integral to an optical fiber and are sensitive to a physical state of the medium that is in contact with the sensor regions. The sensor regions can be encapsulated in a material that changes its physical properties when in contact with carbon dioxide, carbonate, bicarbonate and carbonic acid in an aqueous solution or gaseous carbon dioxide.

In view of the many possible embodiments to which the principles of the disclosed technology may be applied, it should be recognized that the illustrated embodiments are only representative examples and should not be taken as limiting the scope of the disclosure. Alternatives specifically addressed in these sections are merely exemplary and do not constitute all possible alternatives to the embodiments described herein. For instance, various components of systems described herein may be combined in function and use. We therefore claim as our invention all that comes within the scope and spirit of the appended claims.

We claim:

1. A sensor system, comprising:
a plurality of fiber optic sensor regions having associated coatings and configured to be deployed at a plurality of discrete measurement locations, wherein each coating is polystyrene or an acrylate or acrylamide copolymer containing tertiary amine sites which in the presence of $CO_2$ and water vapor reversibly form a salt species according to coating —$NR_2$+$H_2O$+$CO_2$→coating —NH+$R_2HCO_3$—; and
a detection system configured to detect an analyte presence and identify measurement locations associated with the analyte presence.

2. The sensor system of claim 1, wherein the sensor regions are configured to be deployed so that the measurement locations provide coverage of an ocean surface, ocean subsurface, or subsea environment.

3. The sensor system of claim 1, wherein at least one sensor region is associated with a membrane configured to preferentially admit or block a selected substance from an associated sensor region.

4. The sensor system of claim 1, wherein at least one sensor region is sensitive to a total concentration of carbon dioxide, carbonate, bicarbonate or carbonic acid in an aqueous solution.

5. The sensor system of claim 1, wherein at least one sensor region is configured to distinguish between contact with gaseous, liquid or supercritical $CO_2$, aqueous saline solutions and liquid or gaseous hydrocarbons.

6. The sensor system of claim 1, wherein the sensor regions comprise respective long period gratings.

7. The sensor system of claim 1, wherein the sensor regions comprise in-fiber Bragg gratings in an optical fiber that is modified or shaped so that evanescent fields of the optical radiation propagating in a fiber core interact with a medium that surrounds the fiber.

8. The sensor system of claim 1, wherein the sensor regions comprise respective Mach-Zehnder interferometers that comprise respective lengths of photonic crystal fiber spliced into a single mode fiber.

9. The sensor system of claim 1, wherein the sensor regions include a coating selected to exhibit a change in refractive index in response to an analyte.

10. The sensor system of claim 1, wherein at least one sensor region is defined by an enclosure that surrounds a sensor coating such that absorption of an analyte produces a strain in the sensor region.

11. The sensor system of claim 1, further comprising corresponding encapsulating regions situated proximate the sensor regions so as to serve as filters that selectively pass carbon dioxide, carbonate, bicarbonate and carbonic acid to a medium that surrounds the device to the sensor regions.

12. The sensor system of claim 1, wherein at least one of the sensor regions is associated with a membrane that is selectively permeable to $CO_2$, carbonate or bicarbonate ions, or carbonic acid.

13. The sensor system of claim 1, wherein at least one of the sensor regions defines a Fabry-Perot interferometer.

14. A sensor, comprising:
a fiber sensor region; and
a coating situated about the fiber sensor region, and configured to exhibit a change in refractive index in response to a target substance, wherein the coating is polystyrene or an acrylate or acrylamide copolymer containing tertiary amine sites which in the presence of $CO_2$ and water vapor reversibly form a salt species according to coating —$NR_2$+$H_2$+$CO_2$→coating —NH+$R_2HCO_3$—.

15. The sensor of claim 14, wherein the sensor region includes a long period grating.

16. The sensor of claim 14, wherein the coating is enclosed by a radially rigid enclosure and axial enclosures so that absorption of $CO_2$ produces an axial strain in a fiber sensor region.

17. The sensor of claim 16, wherein the fiber sensor region includes a long period grating and the axial strain produces a change in a transmission spectrum.

18. The sensor of claim 17, further comprising:
an optical radiation source;
an optical circulator configured to couple optical radiation from the optical radiation source to the long period grating;
a detection system configured to receive optical radiation transmitted by the long period grating from the optical circulator; and
a processor configured to estimate an analyte concentration based on the received optical radiation.

19. A sensor, comprising:
a plurality of fiber optic sensor regions having associated coatings and configured to be deployed at a plurality of discrete measurement locations,
corresponding encapsulating regions situated proximate the fiber optic sensor regions so as to serve as filters that selectively pass carbon dioxide, carbonate, bicarbonate and carbonic acid to the sensor regions; and
a detection system configured to detect an analyte presence and identify measurement locations associated with the analyte presence.

20. The sensor of claim 19, wherein the sensor regions comprise respective Mach-Zehnder interferometers that include respective lengths of photonic crystal fiber spliced into a single mode fiber.

21. A sensor system, comprising:
a plurality of fiber optic sensor regions having associated coatings and configured to be deployed at a plurality of discrete measurement locations, wherein at least one of the sensor regions is associated with a membrane that is selectively permeable to $CO_2$, carbonate or bicarbonate ions, or carbonic acid;
a detection system configured to detect an analyte presence and identify measurement locations associated with the analyte presence.

* * * * *